(12) United States Patent
Hahn et al.

(10) Patent No.: US 8,745,413 B2
(45) Date of Patent: Jun. 3, 2014

(54) PROTECTED HEALTH CARE DATA MARKETING SYSTEM AND METHOD

(75) Inventors: Christopher Hahn, Bellevue, WA (US); Derek Slager, Issaquah, WA (US)

(73) Assignee: Appature, Inc., Seattle, WA (US)

( * ) Notice: Subject to any disclaimer, the term of this patent is extended or adjusted under 35 U.S.C. 154(b) by 177 days.

(21) Appl. No.: 13/368,266

(22) Filed: Feb. 7, 2012

(65) Prior Publication Data

US 2012/0226916 A1 Sep. 6, 2012

Related U.S. Application Data

(60) Provisional application No. 61/448,529, filed on Mar. 2, 2011.

(51) Int. Cl.
*G06F 21/00* (2013.01)
*G06F 17/30* (2006.01)

(52) U.S. Cl.
CPC ..................................... *G06F 17/30* (2013.01)
USPC ................ 713/193; 713/189; 726/26; 726/27

(58) Field of Classification Search
CPC ....................................................... G06F 17/30
USPC ............................... 713/189, 193; 726/26, 27
See application file for complete search history.

(56) References Cited

U.S. PATENT DOCUMENTS

| | | | |
|---|---|---|---|
| 5,721,831 A | 2/1998 | Waits et al. | |
| 6,071,112 A | 6/2000 | Calvin et al. | |
| 6,073,112 A | 6/2000 | Geerlings | |
| 6,339,795 B1 | 1/2002 | Narurkar et al. | |
| 6,904,409 B1 | 6/2005 | Lambert et al. | |
| 7,660,413 B2 * | 2/2010 | Partovi et al. | 380/33 |
| 7,996,373 B1 * | 8/2011 | Zoppas et al. | 707/694 |
| 8,244,573 B2 | 8/2012 | Hahn et al. | |
| 8,255,370 B1 * | 8/2012 | Zoppas et al. | 707/694 |
| 2004/0103017 A1 | 5/2004 | Reed et al. | |
| 2004/0107386 A1 | 6/2004 | Burdick et al. | |
| 2004/0138958 A1 | 7/2004 | Watarai et al. | |
| 2005/0010477 A1 | 1/2005 | Sullivan et al. | |
| 2005/0131752 A1 | 6/2005 | Gracie et al. | |
| 2005/0159996 A1 | 7/2005 | Lazarus et al. | |
| 2005/0216313 A1 * | 9/2005 | Claud et al. | 705/3 |
| 2005/0261951 A1 | 11/2005 | Tighe | |
| 2006/0206505 A1 | 9/2006 | Hyder et al. | |
| 2007/0033174 A1 * | 2/2007 | Cornacchia | 707/3 |
| 2007/0043761 A1 | 2/2007 | Chim et al. | |

(Continued)

OTHER PUBLICATIONS

Microsoft Office "Microsoft Office Excel 2003 Fast & Easy", published 2004, by Diane Koers, pp. 40-49 & 106-115.

(Continued)

*Primary Examiner* — Chau Le
(74) *Attorney, Agent, or Firm* — Fish & Richardson P.C.

(57) ABSTRACT

Personally-identifying, protected health information ("PHI") is stored in encrypted form in protected data records, and hash values derived from the PHI are stored in associated search records. A healthcare marketer may identify market segments of individuals by querying the search records using hashed query predicates, identifying protected data records based on the search record results, and providing anonymized data-record results to the healthcare marketer. Once a market segment has been anonymously identified, the marketer may cause personalized marketing messages to be generated for individuals in the market-segment without the marketer having been exposed to PHI associated with those individuals.

14 Claims, 13 Drawing Sheets

(56) References Cited

U.S. PATENT DOCUMENTS

| | | |
|---|---|---|
| 2007/0211056 A1 | 9/2007 | Chakraborty et al. |
| 2008/0027995 A1 | 1/2008 | Beigel |
| 2008/0215622 A1* | 9/2008 | Jordan et al. ............... 707/104.1 |
| 2009/0150213 A1 | 6/2009 | Cyr et al. |
| 2009/0177540 A1 | 7/2009 | Quatse |
| 2009/0187461 A1 | 7/2009 | Brignull et al. |
| 2009/0240558 A1 | 9/2009 | Bandy et al. |
| 2010/0094758 A1 | 4/2010 | Chamberlain et al. |
| 2011/0231227 A1 | 9/2011 | Temares et al. |
| 2011/0231410 A1 | 9/2011 | Hahn et al. |
| 2011/0238488 A1 | 9/2011 | Hahn et al. |
| 2012/0232957 A1 | 9/2012 | Hahn et al. |

OTHER PUBLICATIONS

Christen and Gosier, "Quality and Complexity Measures for Data Linkage and Deduplication", 2007, pp. 1-24.

\* cited by examiner

PROTECTED HEALTH CARE DATA MARKETING SYSTEM AND METHOD

CROSS REFERENCE TO RELATED APPLICATIONS

This application claims the benefit of priority to U.S. Provisional Application No. 61/448,529, filed Mar. 2, 2011, titled "PROTECTED HEALTH CARE DATA MARKETING SYSTEM AND METHOD," naming inventors Christopher Hahn and Derek Slager. U.S. Provisional Application No. 61/448,529 is also related to U.S. application Ser. No. 12/689,988, filed Jan. 19, 2010, titled "DATABASE MARKETING SYSTEM AND METHOD," and naming the following inventors: Christopher Hahn, Kabir Shahani, and Derek Slager. The above-cited applications are incorporated herein by reference in their entireties, for all purposes.

FIELD

The present disclosure relates to marketing, and more particularly to computer-managed health-care marketing.

BACKGROUND

Marketers commonly use databases of customers or potential customers (also referred to as "leads") to generate personalized communications to promote a product or service. The method of communication can be any addressable medium, e.g., direct mail, e-mail, telemarketing, and the like.

A marketing database may combine of disparate sources of customer, lead, and/or prospect information so that marketing professionals may act on that information. However, it can be difficult to provide access to a rich set of data in a way that makes sense to the end user of the data (e.g., marketers), as opposed to a database administrator.

Unlike in many fields, marketing activities in the health care field must comply with various privacy rules designed to protect personally-identifying health information. For example, under the United States Health Insurance Portability and Accountability Act ("HIPAA"), protected health information ("PHI") must be treated with special care. According to HIPAA, PHI includes information about health status, provision of health care, or payment for health care that can be linked to a specific individual, such as names, addresses more specific than a state or (in some cases) a range of zip codes, dates (e.g., birth dates, admission and/or discharge dates, death dates, and the like), communications identifiers (e.g., phone and/or fax numbers, email addresses, and the like), account numbers, and the like. Electronic records that include PHI ("EPHI") must comply with various security safeguards, including administrative controls (e.g., restricting access to EPHI to only those employees who have a need for it to complete their job function) and technical controls (e.g., storing EPHI in encrypted form). However, using existing methods, it can be difficult to do effective marketing while still complying with HIPAA-mandated security safeguards.

DESCRIPTION

Figure 1:
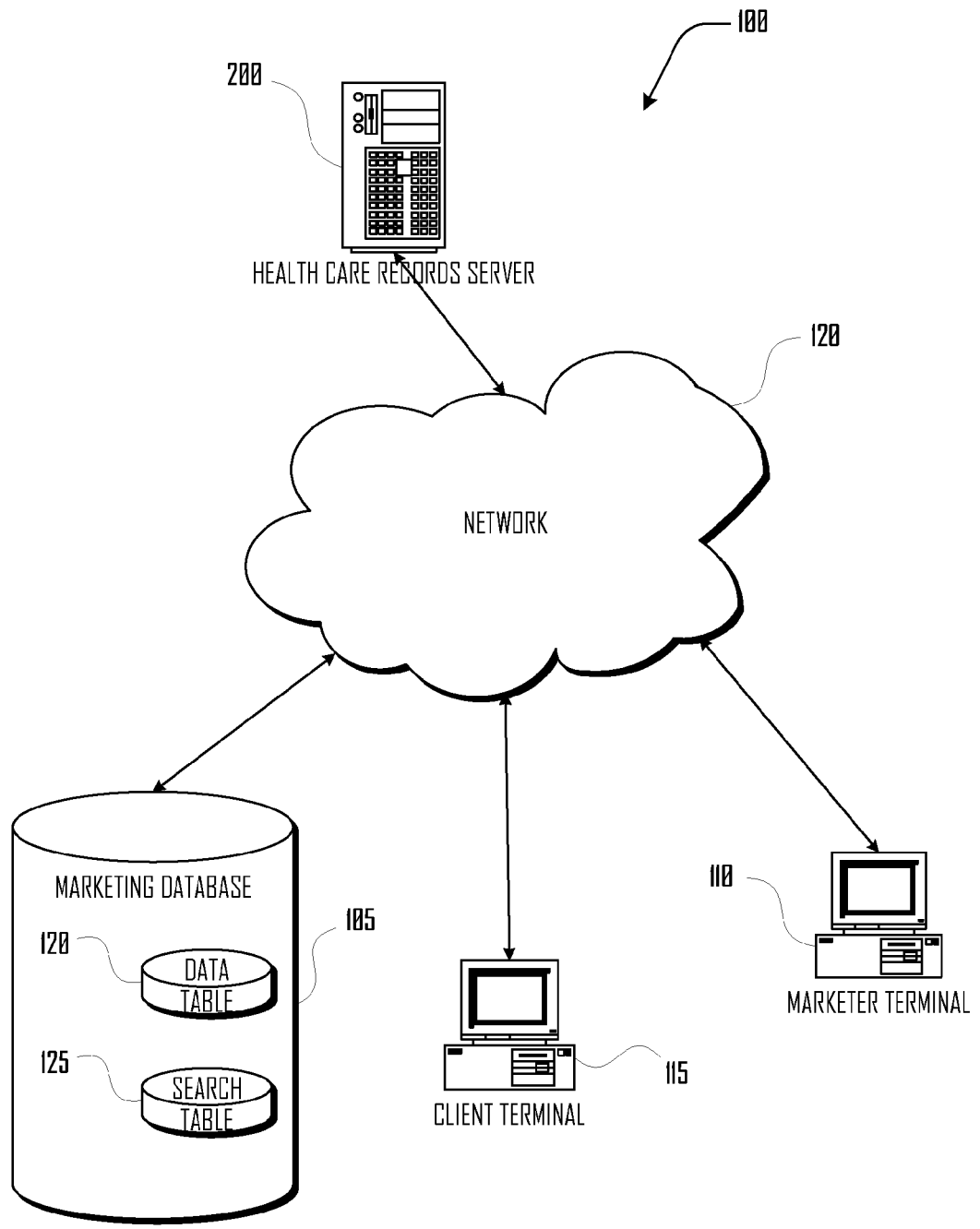
FIG. 1 is a network diagram in accordance with one embodiment.

The detailed description that follows is represented largely in terms of processes and symbolic representations of operations by conventional computer components, including a processor, memory storage devices for the processor, connected display devices, and input devices. Furthermore, these processes and operations may utilize conventional computer components in a heterogeneous distributed computing environment, including remote file Servers, computer Servers and memory storage devices. Each of these conventional distributed computing components is accessible by the processor via a communication network.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise.

As the term is used herein, a "column" refers to a set of data values of a particular type, one for each row of a table. The term "row" refers to a single, implicitly structured data item in a table. The term "field value" refers to the single item that exists at the intersection between one row and one column. The term "field" may be used interchangeably with the term column, unless the context dictates otherwise. The term "record" may be used interchangeably with the term row, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover a10 alternatives, modifications, and equivalents. In alternate embodiments, additional devices or combinations of illustrated devices may be added to or combined without limiting the scope to the embodiments disclosed herein.

FIG. 1 illustrates a number of interconnected devices in accordance with one embodiment. Marketing database 105, marketer terminal 110, client terminal 115, and health care records server 200 are connected to network 120. In various embodiments, network 120 comprises communication switching, routing, and/or data storage capabilities. In various embodiments, network 120 may comprise some or all of the Internet, one or more intranets, and wired and/or wireless network portions. In various embodiments, there may be more than one marketing database 105, and/or marketer terminal 110. Moreover, while FIG. 1 shows a single health care records server 200, in alternative embodiments, the functions, processes, and routines performed by health care records server 200 could be hosted or distributed among two or more different devices. Many embodiments may use multiple devices to comprise one logical device—for example, when health care records server 200 and/or marketing database 105 are executed or hosted in a "cloud computing" environment.

Alternatively, in some embodiments, two or more of health care records server 200, marketer terminal 110, and/or marketing database 105 may be hosted on a single physical computing device. For example, in some embodiments, marketing database 105 may include a process executing on health care records server 200.

Marketing database 105 includes at least a data table 120, which, as discussed below, stores health care records including PHI, and a search table 125, which, as discussed below, facilitates PHI-compliant searching of the health care records.

Marketer terminal 110 and client terminal 115 may include any device that is capable of communicating with health care records server 200, including desktop computers, laptop computers, mobile phones and other mobile devices, PDAs, set-top boxes, and the like.

Figure 2:
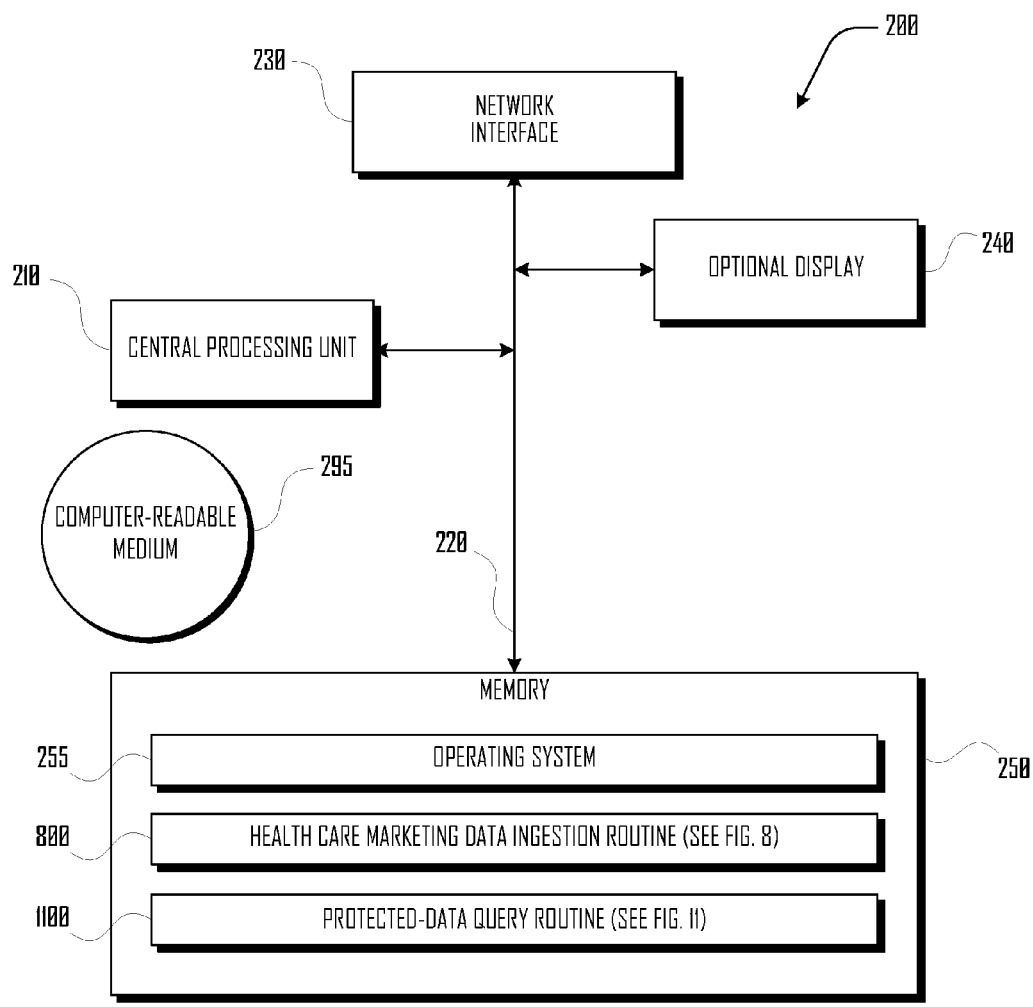
FIG. 2 illustrates one embodiment of a health care records server in accordance with one embodiment.

FIG. 2 illustrates an exemplary health care records server 200. The example system of FIG. 2 depicts a number of subsystems, modules, routines, and engines, some or all of which may by employed in a particular embodiment; the systems, modules, routines, and engines are not, however, limited to those illustrated. Other embodiments could be practiced in any number of logical software and physical hardware components and modules. The modules and components are listed herein merely for example.

Health care records server 200 includes a processing unit 210, a memory 225, and an optional display 240, all interconnected, along with network interface 230, via bus 220. Memory 250 generally comprises a random access memory ("RAM"), a read only memory ("ROM"), and/or a permanent mass storage device, such as a disk drive. In some embodiments, memory 250 may also comprise a local and/or remote database, database server, and/or database service. Memory 250 stores program code for some or all of a health care marketing data ingestion routine 800 (see FIG. 8, discussed below) and protected-data query routine 1100 (see FIG. 11, discussed below). In addition, memory 250 also stores an operating system 255.

These and other software components may be loaded from a non-transient computer readable storage medium 295 into memory 250 of health care records server 200 using a drive mechanism (not shown) associated with a computer readable storage medium 295, such as a floppy disc, tape, DVD/CD-ROM drive, memory card. In some embodiments, software components may also be loaded via the network interface 230 or other transient, non-storage media.

Figure 3:
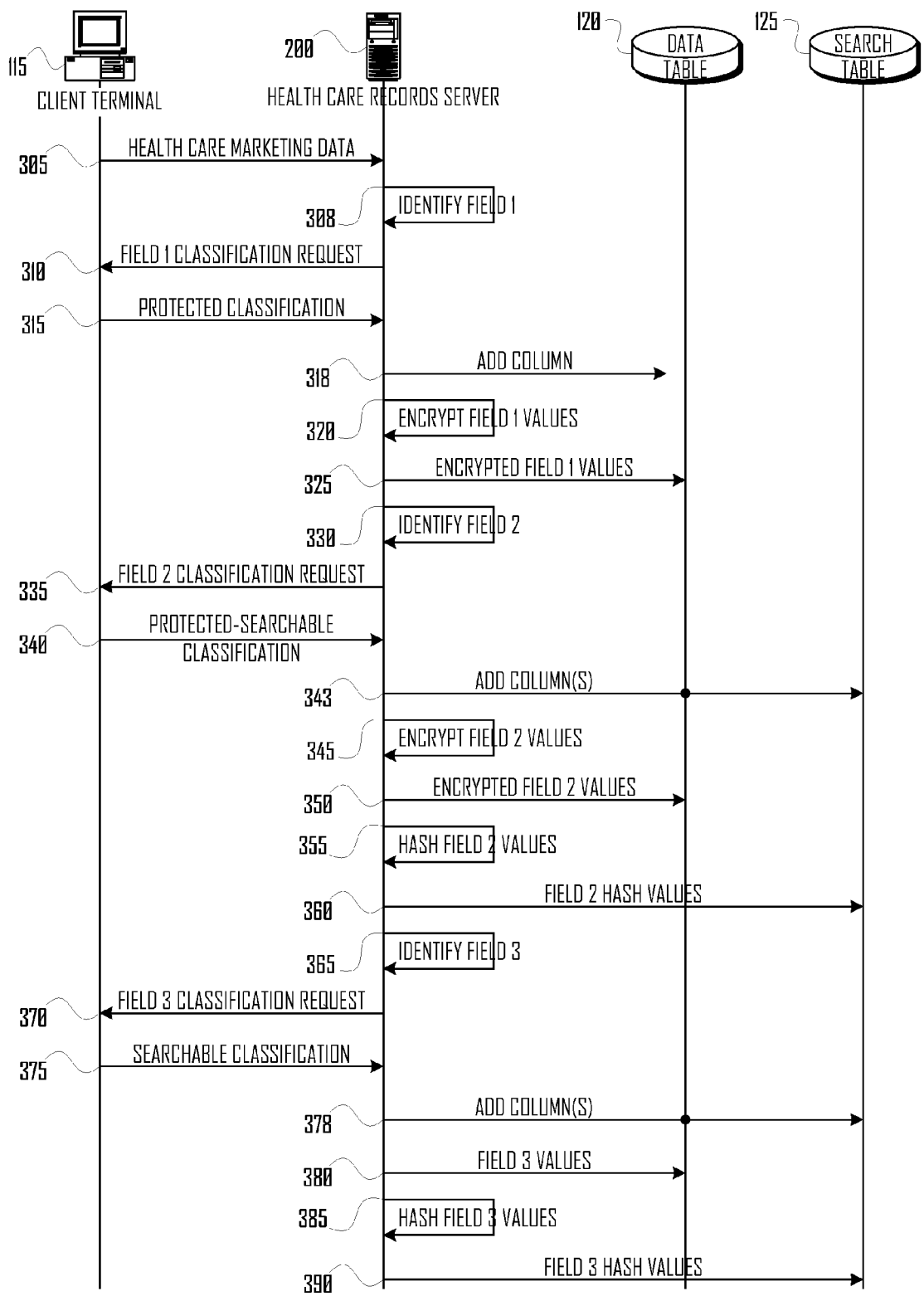
FIG. 3 is a data flow diagram illustrating a marketing record ingestion process in accordance with one embodiment.

FIG. 3 illustrates a high-level data-flow overview of a portion of a healthcare records ingestion process according to one embodiment. Client terminal 115 provides health care records server 200 with health care marketing data 305 including one or more data records related to a patient or other individual or entity who may have associated PHI. For example, in one embodiment, health care records server 200 may provide a web interface by which client terminal 115 can upload marketing data records 305.

Figure 4:
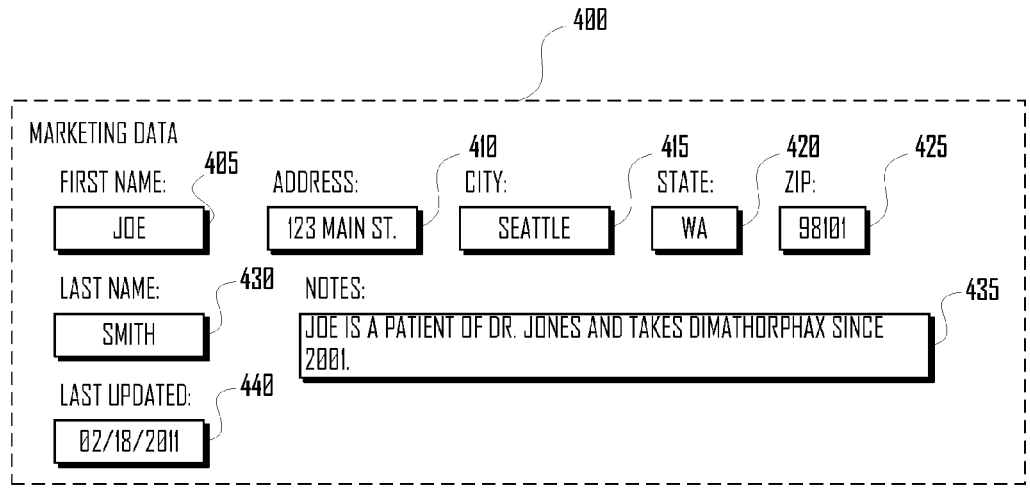
FIG. 4 illustrates a simplified marketing data record in accordance with one embodiment.

For example, FIG. 4 illustrates a simplified marketing data record 400 in accordance with one embodiment. Each data record includes a set of related data values, structured according to several fields or columns. For example, record 400 includes a field value 405 corresponding to a first name column, a field value 430 corresponding to a last name column, a field value 410 corresponding to an address column, a field value 415 corresponding to a city column, a field value 420 corresponding to a state column, a field value 425 corresponding to a zip code column, a field value 435 corresponding to a notes column, and a field value 440 corresponding to a last updated column. In other embodiments, more, fewer, and/or different columns and field values may be employed.

Referring again to FIG. 3, in various embodiments, health care marketing data records 305 may represent current customers, prospective leads, contacts, or the like. Some such types of records (e.g., leads, contacts) may typically represent individual persons. Other such types (e.g. accounts, facilities) may typically represent entities such as associations, hospitals and other health-care facilities, organizations, businesses, and the like. Some record types (e.g., customers) may typically represent both individual persons and entities. In various embodiments, the data record may come from various sources, including mailing lists, product registrations, public databases, membership lists, trade shows, and the like.

Health care records server 200 receives the field of patient data 305 and identifies a first field 308 or column in the structure of data records 305. For example, in one embodiment, health care records server 200 may identify a first or last name field in the structure of data records 305. In one embodiment, health care records server 200 sends a request 310 for client terminal 115 to classify the first field at least as protected/not protected and searchable/not-searchable. For example, in one embodiment, health care records server 200 may provide a web interface indicating the first field and prompting the operator of client terminal 115 to select a classification for the first field. In some embodiments, additional classifications may be employed. In the illustrated embodiment, fields are assumed to be not searchable unless otherwise specified.

Client terminal 115 determines (not shown) that the field in question should be protected, but not searchable, and sends an appropriate classification 315 to health care records server 200. In some embodiments, the classification of fields may be performed by an operator of client terminal 115. In other embodiments, client terminal 115 may store a pre-determined classification for each field of data records 305. In still other embodiments, health care records server 200 may store a pre-determined classification for each field of data records 305 and/or health care records server 200 may automatically determine an initial classification based on the name of the field, the field values of the field, or the like.

Based on the protected classification 315 assigned to the first field, health care records server 200 adds an encrypted first field 318 to the structure of data table 120 and encrypts field values 320 corresponding to the first field in data records 305. For example, in one embodiment, health care records server 200 may encrypt field values 320 according to a symmetric-key encryption standard such as Advanced Encryption Standard ("AES")-128, AES-192, AES-256, or the like. Health care records server 200 stores the encrypted field values 325 in the encrypted first field of data table 120.

Figure 5:
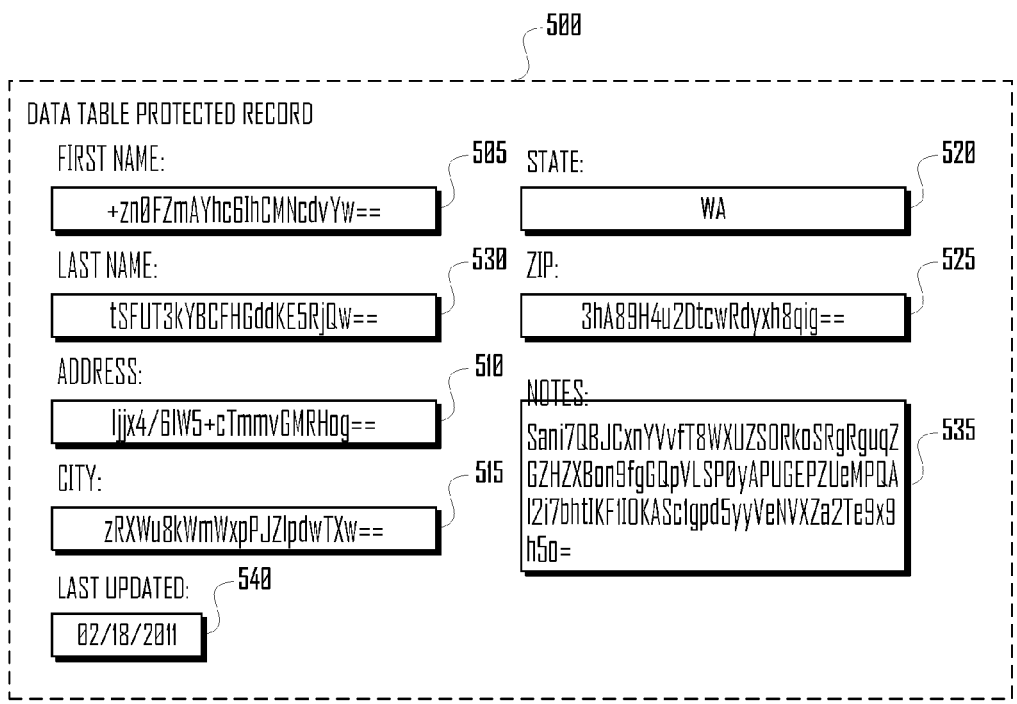
FIG. 5 illustrates a simplified data table record in accordance with one embodiment.

For example, FIG. 5 illustrates a simplified data table protected record 500 in accordance with one embodiment.

Record 500 includes an encrypted field value 505 corresponding to a protected first name column, an encrypted field value 530 corresponding to a protected last name column, an encrypted field value 510 corresponding to a protected address column, an encrypted field value 515 corresponding to a protected city column, an encrypted field value 525 corresponding to a zip code column, and an encrypted field value 535 corresponding to a notes column. In other embodiments, more, fewer, and/or different columns and field values may be employed.

Referring again to FIG. 3, health care records server 200 identifies a second field 330 or column in the structure of data records 305. For example, in one embodiment, health care records server 200 may identify a state or zip code field in the structure of data records 305. In one embodiment, health care records server 200 sends a request 335 for client terminal 115 to classify the second field at least as protected/not protected and searchable/not-searchable.

Client terminal 115 determines (not shown) that the field in question should be protected and searchable and sends an appropriate classification 340 to health care records server 200. In some embodiments, the classification of fields may be performed by an operator of client terminal 115.

Based on the protected-searchable classification 340 assigned to the second field, health care records server 200 adds columns 343 to the structure of data table 120 and search table 125. Health care records server 200 encrypts field values 345 corresponding to the second field in data records 305. Health care records server 200 stores the encrypted field values 350 in the encrypted second field of data table 120.

Based on the protected-searchable classification 340 assigned to the second field, health care records server 200 determines cryptographic or one-way hash values 355 corresponding to the second-field values in data records 305. Health care records server 200 stores the second-field hash values 360 in the corresponding field of search table 125.

Figure 6:
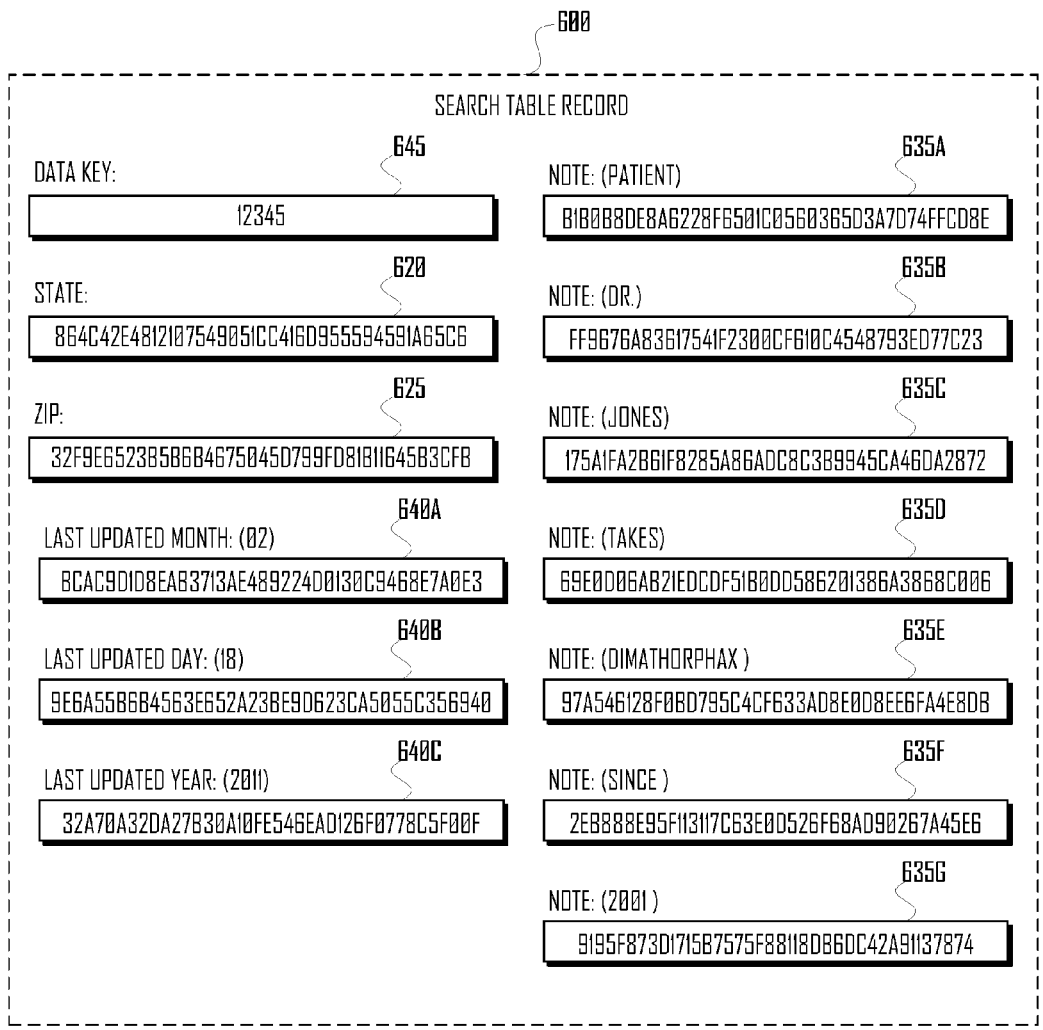
FIG. 6 illustrates a simplified search table record in accordance with one embodiment.

For example, FIG. 6 illustrates a simplified search table record 600 in accordance with one embodiment. Record 600 includes foreign key 645 referring to the corresponding data table record; a hash value 620 corresponding to a state column; a hash value 625 corresponding to a zip code column; hash values 640A-C corresponding to month, day, and year last-updated columns, and hash values 635A-G corresponding to searchable notes columns. In other embodiments, more, fewer, and/or different columns and field values may be employed.

As the terms are used herein, a "cryptographic hash" value, "one-way hash" value, or simply "hash value" refers to a digest obtained by supplying a plaintext field value to a cryptographic hash function that returns a fixed-size bit string (the hash value). A typical cryptographic function is chosen such that it is easy to compute the hash value for any given input, it is infeasible to find an input that has a given hash, it is infeasible to modify an input without its hash value being changed, and it is infeasible to find two different inputs with the same hash. For example, in one embodiment, health care records server 200 may utilize the SHA-1 cryptographic hash function to obtain hash values such as second field hash values 360. In other embodiments, other hash functions may be utilized, e.g., MD5, MD6, SHA-0, SHA-2, SHA-3, or the like. In some embodiments, the hash function may be used in connection with a salt.

Referring again to FIG. 3, health care records server 200 identifies a third field 365 or column in the structure of data records 305. For example, in one embodiment, health care records server 200 may identify a last-updated field in the structure of data records 305. In one embodiment, health care records server 200 sends a request 370 for client terminal 115 to classify the third field at least as protected/not protected and searchable/not-searchable.

Client terminal 115 determines (not shown) that the field in question should be non-protected and searchable and sends an appropriate classification 375 to health care records server 200. In some embodiments, the classification of fields may be performed by an operator of client terminal 115.

Based on the non-protected/searchable classification 375 assigned to the third field, health care records server 200 adds columns 378 to the structure of data table 120 and search table 125. Health care records server 200 stores the plain-text field values 380 in the corresponding field of data table 120. Health care records server 200 determines cryptographic or one-way hash values 385 corresponding to the third field values in data records 305. Health care records server 200 stores the third field hash values 390 in the corresponding field of search table 125.

In some embodiments, the process of identifying and classifying fields, and storing data accordingly may continue until all fields of data records 305 have been processed.

Figure 7:
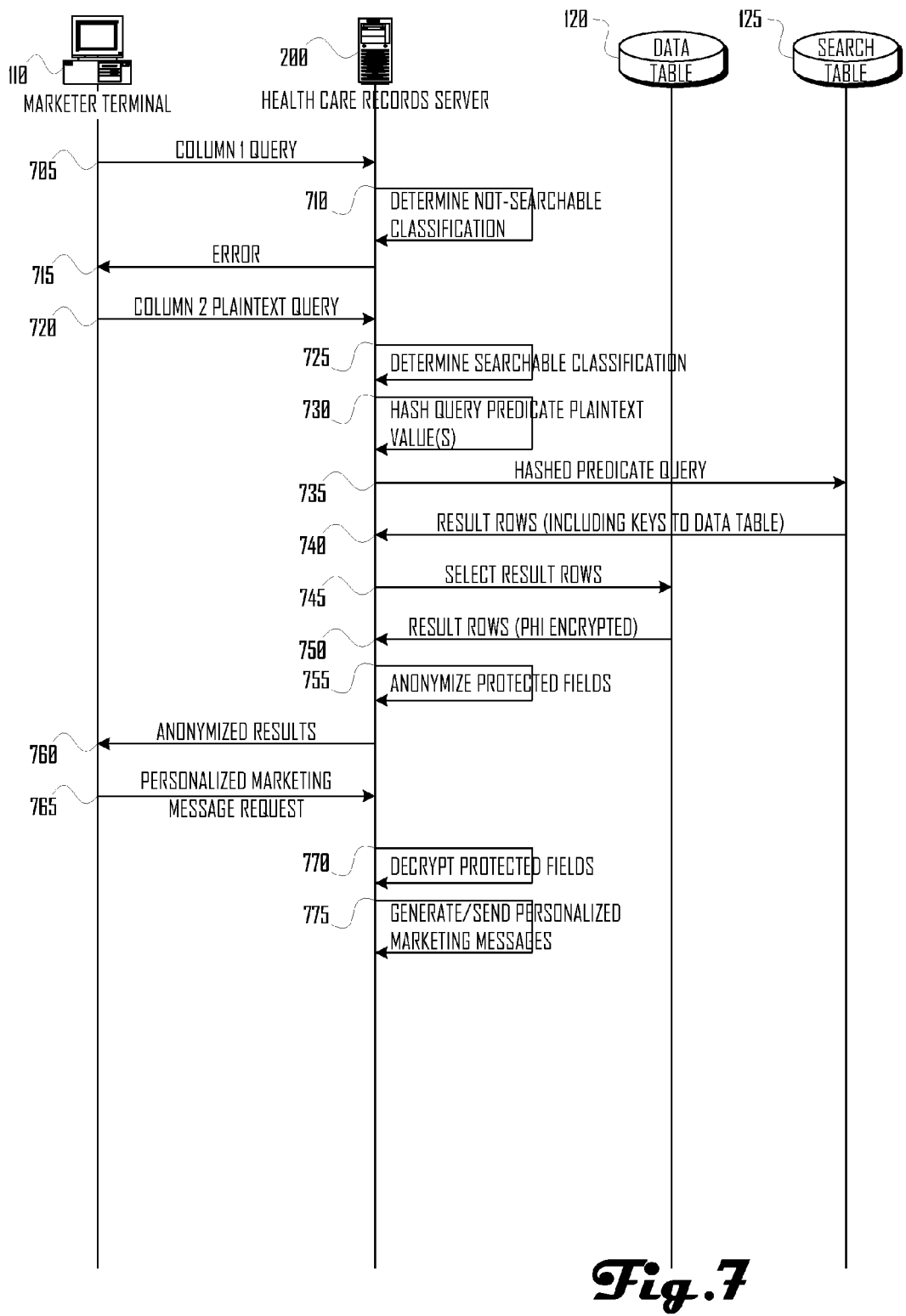
FIG. 7 illustrates a data flow overview of a portion of a healthcare records protected search process according to one embodiment

FIG. 7 illustrates a high-level data flow overview of a portion of a healthcare records protected search process, such as may be employed following the ingestion process shown in FIG. 3 (discussed above) according to one embodiment. Marketer terminal 110 sends to health care records server 200 a query 705 referencing a first column of health care marketing data stored in data table 120. For example, in one embodiment, marketer terminal 110 may send a query to locate one or more records according to values in a first or last name column, such as SELECT*FROM DataTable WHERE LastName="Smith"

Health care records server 200 determines that the first column (e.g. LastName) is classified as not searchable 710 and accordingly sends an error indication 715 to marketer terminal 110 indicating that the query 705 references a non-searchable field.

Marketer terminal 110 sends to health care records server 200 a query 720 referencing a second column of health care marketing data stored in data table 120. For example, in one embodiment, marketer terminal 110 may send a query to locate one or more records according to values in a state or zip code column, such as SELECT*FROM DataTable WHERE State="WA"

Health care records server 200 determines that the second column (e.g., State) is classified as searchable 725 and obtains one-way hash values from query predicate values that reference searchable fields, the hash values being obtained using the same cryptographic hash function that was used to prepare data values for storage in search table 125. For example, in the above illustrative query, the query predicate restricts result rows to those where the searchable field named State has a value of "WA". Accordingly, health care records server 200 would obtain a hash value from the string "WA". In one embodiment, using the SHA-1 hash function, health care records server 200 may obtain a hash value of "864c42e4812107549051 cc416d955594591a65c6."

Health care records server 200 then queries search table 125 using the hashed predicate value. For example, continuing the illustrative query discussed above, health care records server 200 may perform a hashed-predicate query such as SELECT DataKey FROM SearchTable
WHERE State="864c42e4812107549051 cc416d955594591a65c6"

From search table 125, health care records server 200 obtains one or more search-table result rows 740 identified by the hashed-predicate query 735, the one or more search-table result rows 740 including foreign keys referencing the corresponding records in data table 120.

Using the foreign keys from the search-table result rows 740, health care records server 200 sends a query 745 to data table 120, which returns data-table result rows 750, including one or more columns of protected PHI in encrypted form.

Health care records server 200 anonymizes the data-table result rows 755, such that the anonymized results 760 that are sent to marketer terminal 110 do not reveal any PHI to the marketer. For example, name and/or address fields may be displayed with asterisks in place of PHI data. Nonetheless, the marketer may be able to work with the anonymized results, sending a request 765 to health care records server 200 to send one or more personalized marketing messages to individuals whose records are represented in anonymized results 760.

Health care records server 200 decrypts PHI field values that are stored in data-table result rows 750 and uses the decrypted field values to generate and send (or cause to be sent) personalized marketing messages to the individuals identified in data-table result rows 750. Thus, personalized marketing activities may be carried out at marketer terminal 110 without revealing any protected PHI to a marketer, and even without decrypting any PHI except during the automated process of generating a personalized marketing message.

Figure 8:
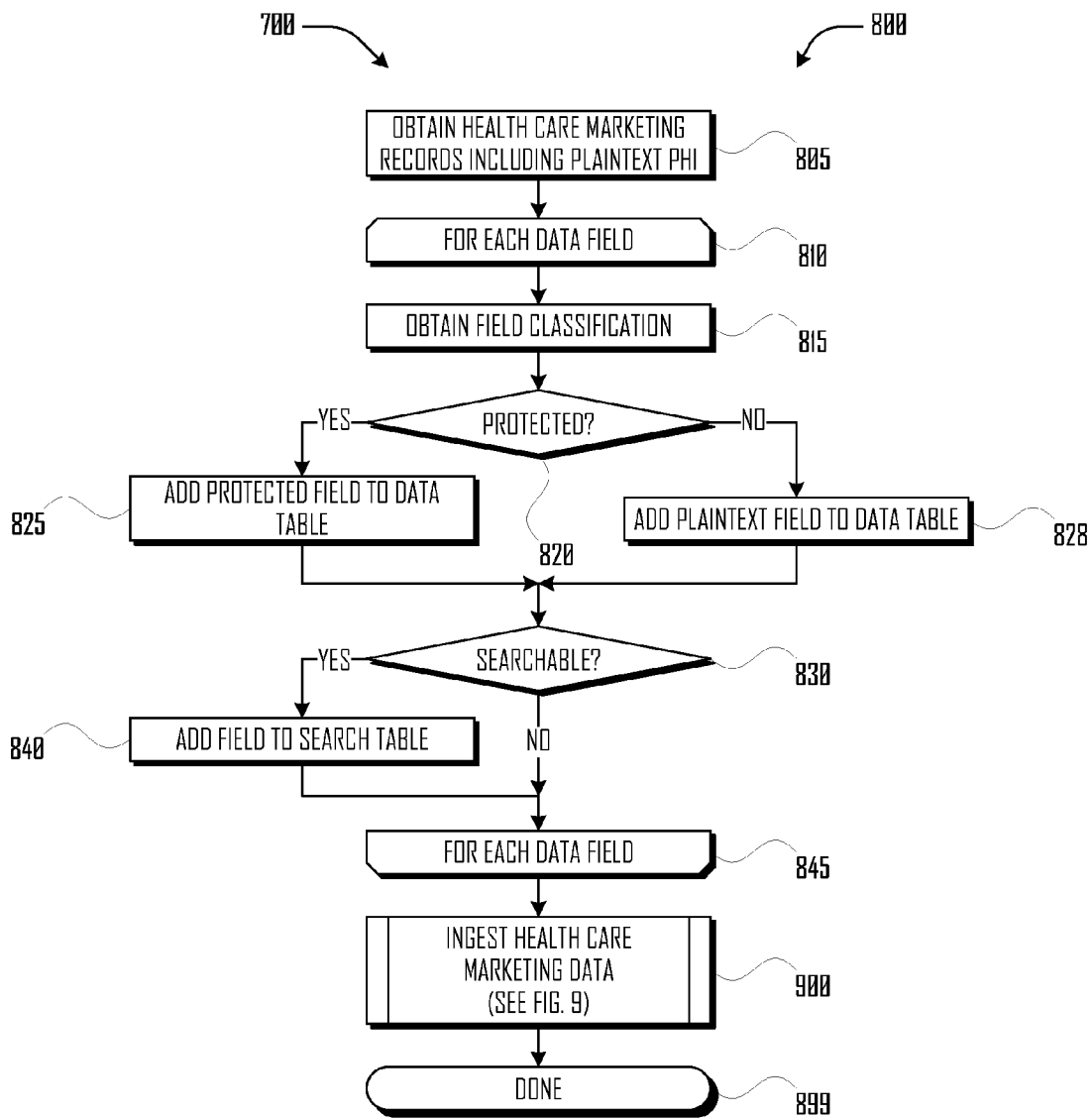
FIG. 8 illustrates a health care marketing data ingestion routine in accordance with one embodiment.

FIG. 8 illustrates a health care marketing data ingestion routine 800, such as may be performed by health care records server 200 in accordance with one embodiment. In block 805, routine 800 obtains a plurality of health care marketing records (e.g., simplified marketing data records 400, as illustrated in FIG. 4 and discussed above), including one or more fields of (typically plaintext) PHI. In some embodiments, the health care marketing records may be obtained via a network from client terminal 115. In other embodiments, the health care marketing records may be obtained via a storage medium or via other means.

In some embodiments, the health care marketing records may be cleaned, de-duplicated, and/or otherwise pre-processed prior to being stored in data table 120, as discussed below.

Beginning in opening loop block 810, routine 800 iterates over each field or column in the structure of the health care marketing records obtained in block 805.

In block 815, routine 800 obtains a field classification for the current field. For example, in one embodiment, routine 800 may obtain a classification indicating that the current field is combination of searchable/non-searchable and protected/non-protected. In some embodiments, routine 800 may obtain a classification via a web interface indicating the first field and prompting the operator of client terminal 115 to select a classification for the first field. In other embodiments, routine 800 may consult a pre-determined classification for the current field. In still other embodiments, routine 800 may automatically determine an initial classification based on the name of the current field, the field values of the current field, or the like.

In decision block 820, routine 800 determines, according to the classification received in block 815, whether the current field includes PHI or other data that much be protected. If the classification indicates that the current field must be protected, then in block 825, routine 800 adds to a data table (e.g., data table 120) a protected field corresponding to the current data field. If the classification indicates that the current field need not be protected, then in block 828, routine 800 adds to a data table (e.g., data table 120) a plaintext field corresponding to the current field.

In decision block 830, routine 800 determines, according to the classification obtained in block 815, whether the current field is to be searchable. If the classification indicates that the current field should be searchable, then in block 840, routine 800 adds to a search table (e.g., search table 125) a field corresponding to the current field.

In ending block 845, routine 800 loops back to block 810 to process the next field or column (if any) in the structure of the health care marketing records obtained in block 805.

In subroutine block 900 (see FIG. 9, discussed below), routine 800 ingests the data included in the health care marketing records obtained in block 805. During the ingestion process, the data is populated into the protected data table and search table that were structured as described above in relation to blocks 810 to 845. Routine 800 ends in block 899.

Figure 9:
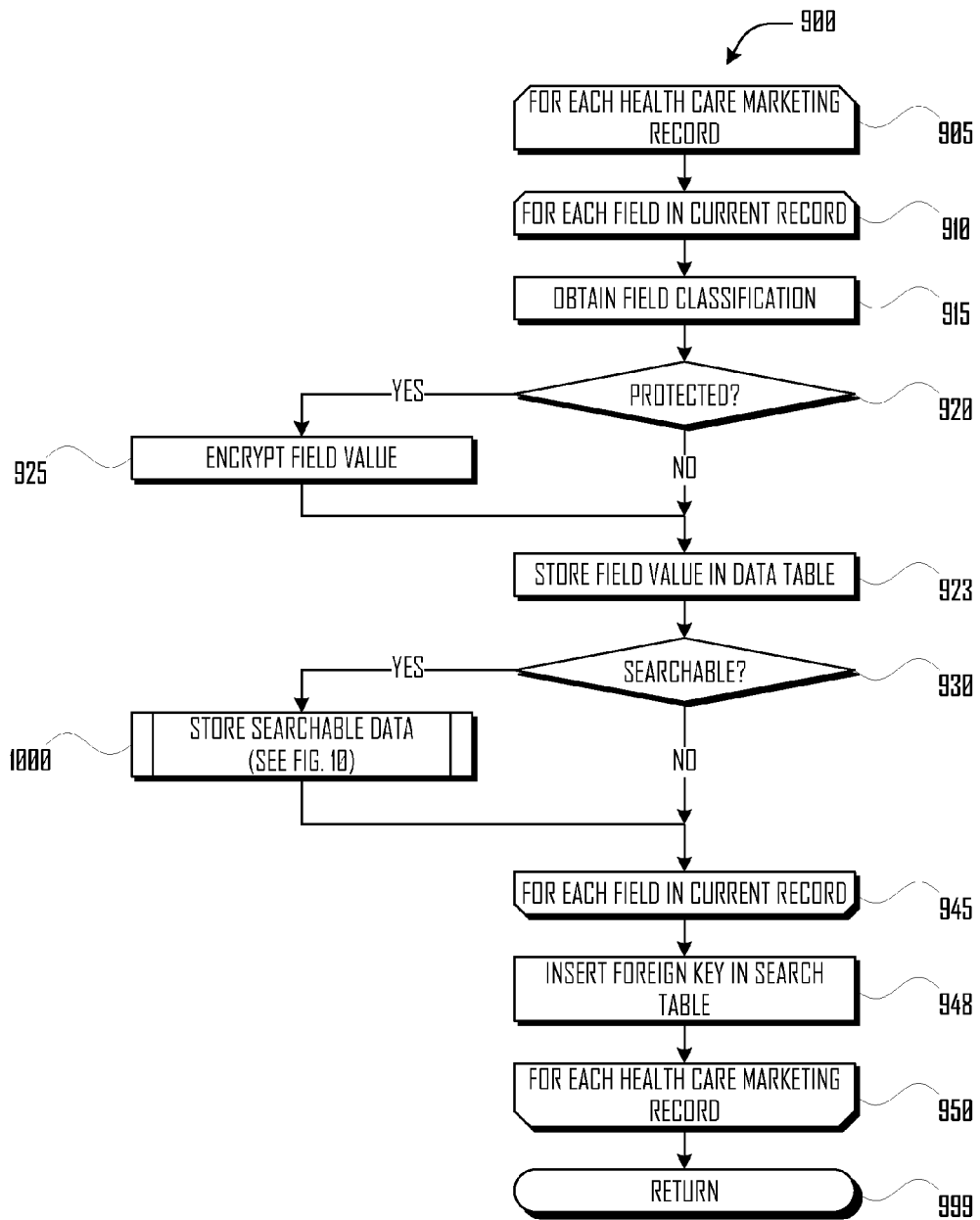
FIG. 9 illustrates a health care marketing data ingestion subroutine in accordance with one embodiment.

FIG. 9 illustrates health care marketing data ingestion subroutine 900 in accordance with one embodiment. Beginning in opening loop block 905, subroutine 900 iterates over each record of a plurality of health care marketing records.

Beginning in opening loop block 910, subroutine 900 iterates over each field or column in the structure of the current health care marketing record.

In block 915, routine 900 obtains a field classification for the current field. For example, in one embodiment, routine 900 may obtain a classification indicating that the current field is combination of searchable/non-searchable and protected/non-protected.

In decision block 920, routine 900 determines whether the value of the current field includes PHI or other data that must be protected according to the classification obtained in block 915. If the classification indicates that the current field value must be protected, then in block 925, routine 900 encrypts the field value of the current field of the current record.

In block 923, subroutine 900 stores the field value (in plaintext form if not protected, in encrypted form if protected) in the field of the protected data table that corresponds to the current field.

In decision block 930, routine 900 determines, according to the classification received in block 915, whether the current field value is to be searchable. If the classification indicates that the current field should be searchable, then in subroutine block 1000 (see FIG. 10, discussed below), data corresponding to the current field value is stored in a search table (e.g., search table 125).

In ending loop block 945, subroutine 900 iterates back to block 910 to process the next field or column (if any) in the structure of the current health care marketing record.

In block 948, subroutine 900 inserts a foreign key into the search table record corresponding to the current record, the foreign key referencing the data table record corresponding to the current record.

In ending block 950, subroutine 900 loops back to block 905 to process the next record (if any) of the plurality of health care marketing records. Subroutine 900 ends in block 999.

Figure 10:
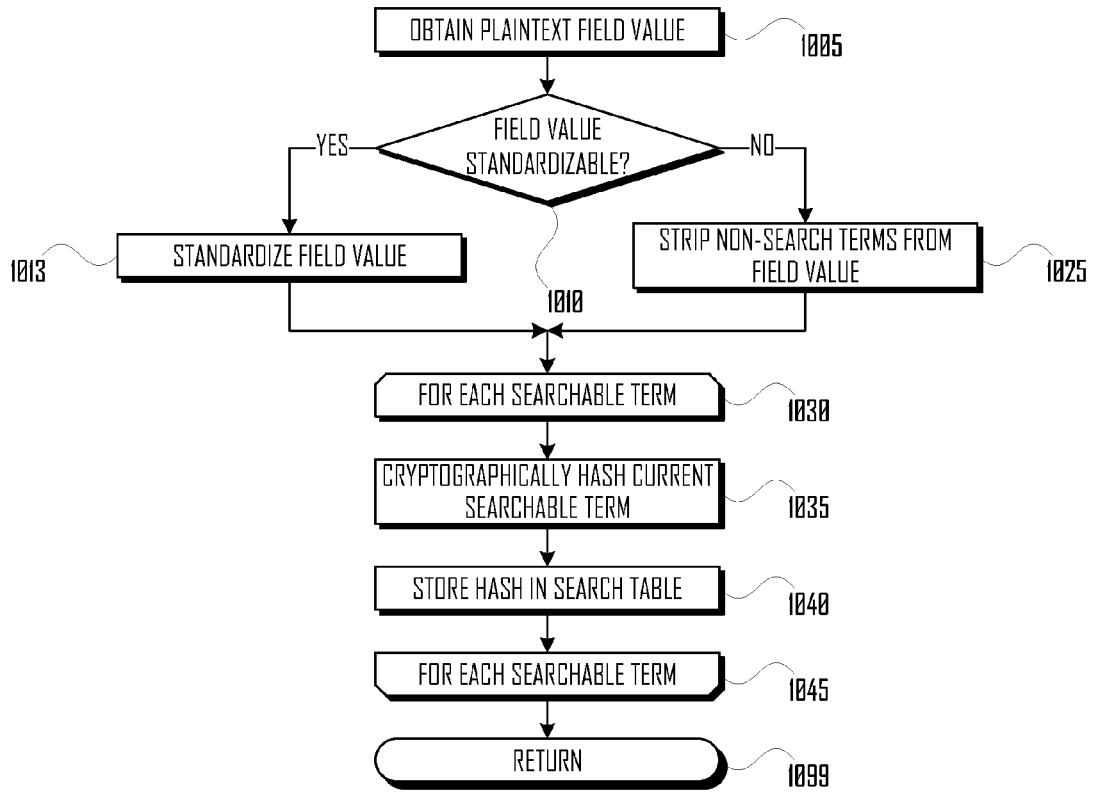
FIG. 10 illustrates a PHI search table storage subroutine in accordance with one embodiment.

FIG. 10 illustrates a PHI search table storage subroutine 1000 in accordance with one embodiment. In block 1005, subroutine 1000 obtains a field plaintext value for the field being processed.

In decision block 1010, subroutine 1000 determines whether the field value represents normalizable and/or standardizable data. If so, then in block 1013, subroutine 1000 standardizes the field value obtained in block 1005. For example, a city, state, zip code, or other address field may be normalizable according to United Stated Post Office standards. Similarly, a title field might use standardized abbreviations for "Dr." or other common titles. In some embodiments, such a normalization/standardization process might be accomplished prior to subroutine 1000, possibly in a batch pre-processing data cleansing and/or normalization process.

In some embodiments, subroutine 1000 may perform additional processing on the field value. For example, in some embodiments, the value of a zip code field may be truncated to the first three digits, the last two digits replaced with zeros or other anonymized data, or the like.

However, in decision block 1010, subroutine 1000 may determine that the field value does not represent normalizable and/or standardizable data. For example, the field value may include free-form text, such as a notes field or the like. When the field value includes such data, then in block 1025, subroutine 1000 strips non-search terms from the field value. For example, in one embodiment, subroutine 1000 may strip out non-search terms such as "the," "and," "is," "have," "can," "or," "not," "it," "its," "of," "by," "but," "as," "do," "for," "had," "has," "in," or other like terms that are unlikely to be used as search terms. In some embodiments, subroutine 1000 may also strip out identifying terms, such as doctor and patient names, addresses, and other identifying information that may be determined from the record of which the current field is a part.

For example, when processing the notes field shown in FIG. 4, subroutine 1000 might strip out non-search terms such as those enumerated above, and subroutine 1000 might also strip out identifying terms such as the value of the first name field 405 ("Joe"), as well as the value of any other protected fields (e.g., last name 430, address 410, and the like) that may be included in the free-form text of the notes field 435.

Referring again to FIG. 10, beginning in opening loop block 1030, subroutine 1000 iterates over each searchable term in the field value obtained in block 1005 and processed by blocks 1013 or 1025. In some cases, the field value may include only a single searchable term, such as when the field value represents a state or a zip code. In other cases, such as when the field value represents free-form text or a date (which may include some or all of a day, month, year, and the like), the field value may include multiple searchable terms.

In block 1035, subroutine 1000 provides the current searchable term of the processed field value to a cryptographic hash function (e.g., SHA-1) to obtain a hash value corresponding to the current searchable term. In block 1040, subroutine 1000 stores the hash value in a corresponding field of search table 125. In ending loop block 1045, subroutine 1000 iterates back to block 1030 to process the next searchable term (if any). Subroutine 1000 ends in block 1099.

For example, the results of subroutine 1000 may be observed by comparing data record 400 (as illustrated in FIG. 4) and search table record 600 (as illustrated in FIG. 6). The "atomic" or singleton searchable field values 420 ("WA") and 425 ("98101") correspond to singleton search table field values 620 and 625, which store hash values corresponding to field values 420 and 425. (In some embodiments, if the zip code has been further anonymized, as discussed above in reference to block 1013, then searchable field value 425 may be "98100", "981**", or simply "981".)

Slightly more complex are the values of the last updated field 440 and the notes field 435. In both cases, one field in the original healthcare marketing data corresponds to several search fields in search table 600. As illustrated, the value of the last updated field 440 has been divided into a last updated month value 640A, a last updated day value 640B, and a last updated year value 640C, which may facilitate searches by date and/or date range.

Similarly, the value of notes field 435 has been stripped of a number of non-search "stem" words (specifically, "is," "a," "of," and "and"), and the notes field 435 has also been stripped of the value of first name field 405, which is a protected field, as it includes PHI ("Joe"). Consequently, notes field 435 corresponds to notes fields 635A-G in search table record 600, which may facilitate searching by terms that are substrings of the value of field 435.

Figure 11:
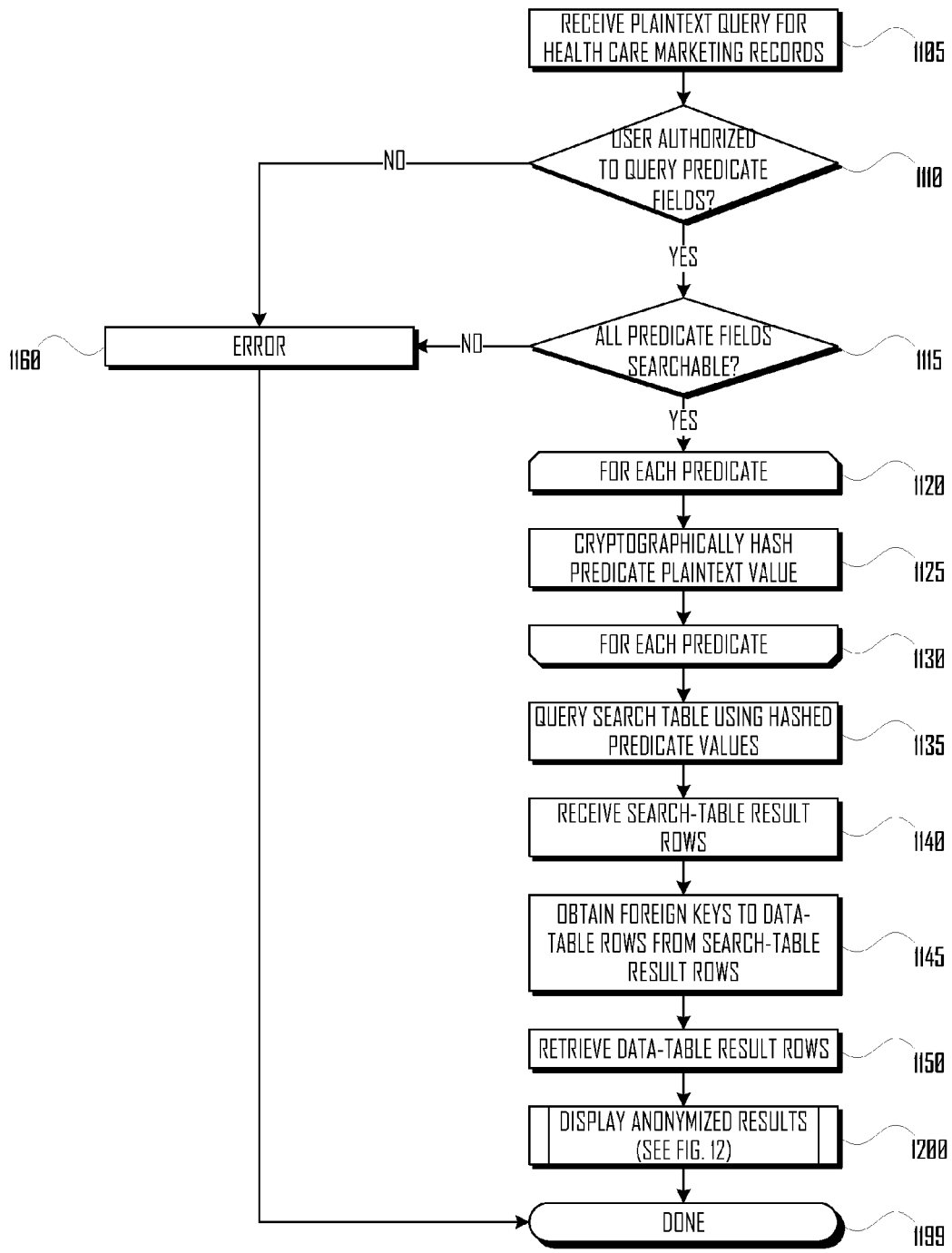
FIG. 11 illustrates a protected-data query routine in accordance with one embodiment.

FIG. 11 illustrates a protected-data query routine 1100, such as may be performed by health care records server 200 in accordance with one embodiment. In block 1105, routine 1100 receives a query describing a set of health care marketing records stored in data table 120. For example, in one embodiment, routine 1100 may receive a query via a web interface from a marketer terminal 110.

In decision block 1110, routine 1100 determines whether the user who submitted the query is authorized to query the predicate fields referenced in the query, and in decision block 1115, routine 1100 determines whether all predicate fields are searchable. If the result of either determination is negative, then routine 1100 throws an error in block 1160.

For example, in one embodiment, a user of a marketer terminal 110 may submit a query to locate one or more records according to values in a first or last name column, such as SELECT*FROM DataTable WHERE LastName="Smith"

In some embodiments, this query may generate an error at decision block 1110 (if that particular marketer is not allowed to search by the last name field) and/or decision block 1115 (if the LastName field is not searchable).

By contrast, in other embodiments, a user of a marketer terminal 110 may submit a query to locate one or more records according to values in a searchable column that the user is authorized to query, such as SELECT*FROM DataTable
WHERE State="WA" and LastUpdatedYear="2011"

When the submitted query is valid and authorized, beginning in opening loop block 1120, routine 1100 iterates over each predicate in the submitted query. For example, in the illustrative embodiment discussed immediately above, routine 1100 would iterate over two predicates:

State="WA"; and
LastUpdatedYear="2011"

In block 1125, routine 1100 cryptographically hashes the predicate value of the current predicate to obtain a hashed predicate value. For example, in one embodiment, routine 1100 may obtain a hashed predicate value of "864c42e4812107549051 cc416d955594591a65c6" for a predicate value of "WA," and routine 1100 may obtain a hashed predicate value of "32a70a32da27b30a10fe546ead126f0778c5f00f" for the predicate value of "2011."

In ending loop block 1130, routine 1100 iterates back to block 1120 to process the next query predicate (if any).

In block 1135, routine 1100 queries search table 125 using the hashed predicate values, and in block 1140, routine 1100 receives a set of one or more search-table result rows. For example, in one embodiment, routine 1100 may query search table 125 using a hashed-predicate query such as SELECT DataKey FROM SearchTable
WHERE State="864c42e4812107549051
cc416d955594591a65c6" AND
LastUpdatedYear=
"32a70a32da27b30a10fe546ead126f0778c5f00f"

In block 1145, routine 1100 obtains, from the search-table result rows, foreign keys referencing corresponding data records in data table 120. In block 1150, using the foreign keys from the search-table result rows, routine 1100 retrieves corresponding data-table result rows from data table 120, the data-table result rows including one or more columns of protected PHI in encrypted form.

In subroutine block 1200, routine 1100 displays anonymized results (e.g., via a web interface) to the user of marketer terminal 110. Routine 1100 ends in block 1199.

Figure 12:
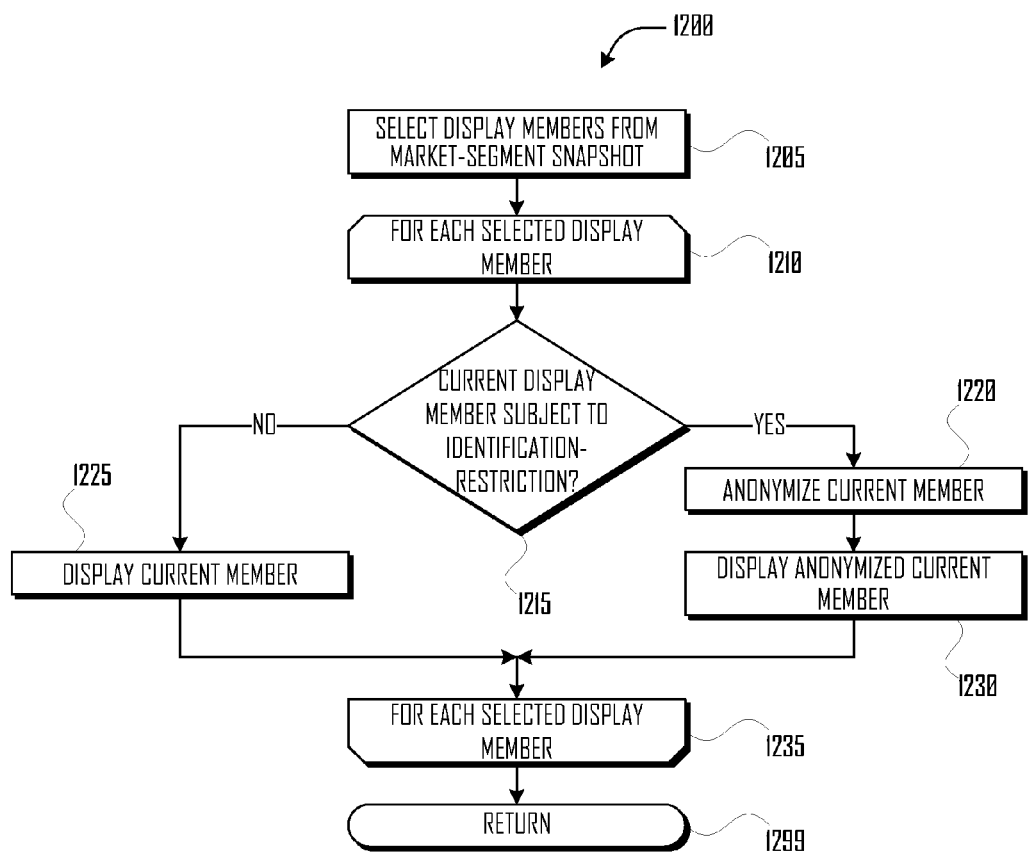
FIG. 12 illustrates a protected-data query routine in accordance with one embodiment.

FIG. 12 illustrates an anonymized results display subroutine 1200 in accordance with one embodiment. In block 1205, subroutine 1200 selects some or all of the members of a set of data-table result rows. For example, in one embodiment, a large set of data-table result rows may be displayed in a series of "pages," each displaying a certain number ("X") of records. Thus, in such cases, subroutine 1200 may select the Nth set of X members for display on the current page, where "N" refers to the number of the current page. In other embodiments, all members of the set of data-table result rows may be selected for display. In still other embodiments, members may be selected according to user-provided or other criteria (e.g., all members of a certain type).

Beginning in block 1210, subroutine 1200 iterates over each member of the set of data-table result rows that has been selected for display. In decision block 1215, subroutine 1200 determines whether the current member of the set of data-table result rows is subject to an identification restriction. If subroutine 1200 determines that the current member is not subject to an identification-restriction, subroutine 1200 provides the member record for non-anonymous display in block 1225.

If, however, subroutine 1200 determines that the current member is subject to an identification-restriction, subroutine 1200 anonymizes the member record in block 1220 and provides the anonymized member record for display in block 1230.

In some embodiments, subroutine 1200 may further associate an anonymous unique identifier with the member so that the marketer may send marketing messages (even personalized marketing messages) to the individual associated with the member record without the individual's identifying information being exposed to the marketer. Thus, in some embodiments, while complying with HIPAA and/or other identification-restrictions, a marketer may market to a market-segment without the marketer being exposed to personally-identifying information about individuals in the market segment.

In block 1235, subroutine 1200 cycles back to block 1210 to process the next selected display member. Once all selected display members have been processed, subroutine 1200 ends in block 1299.

Figure 13:
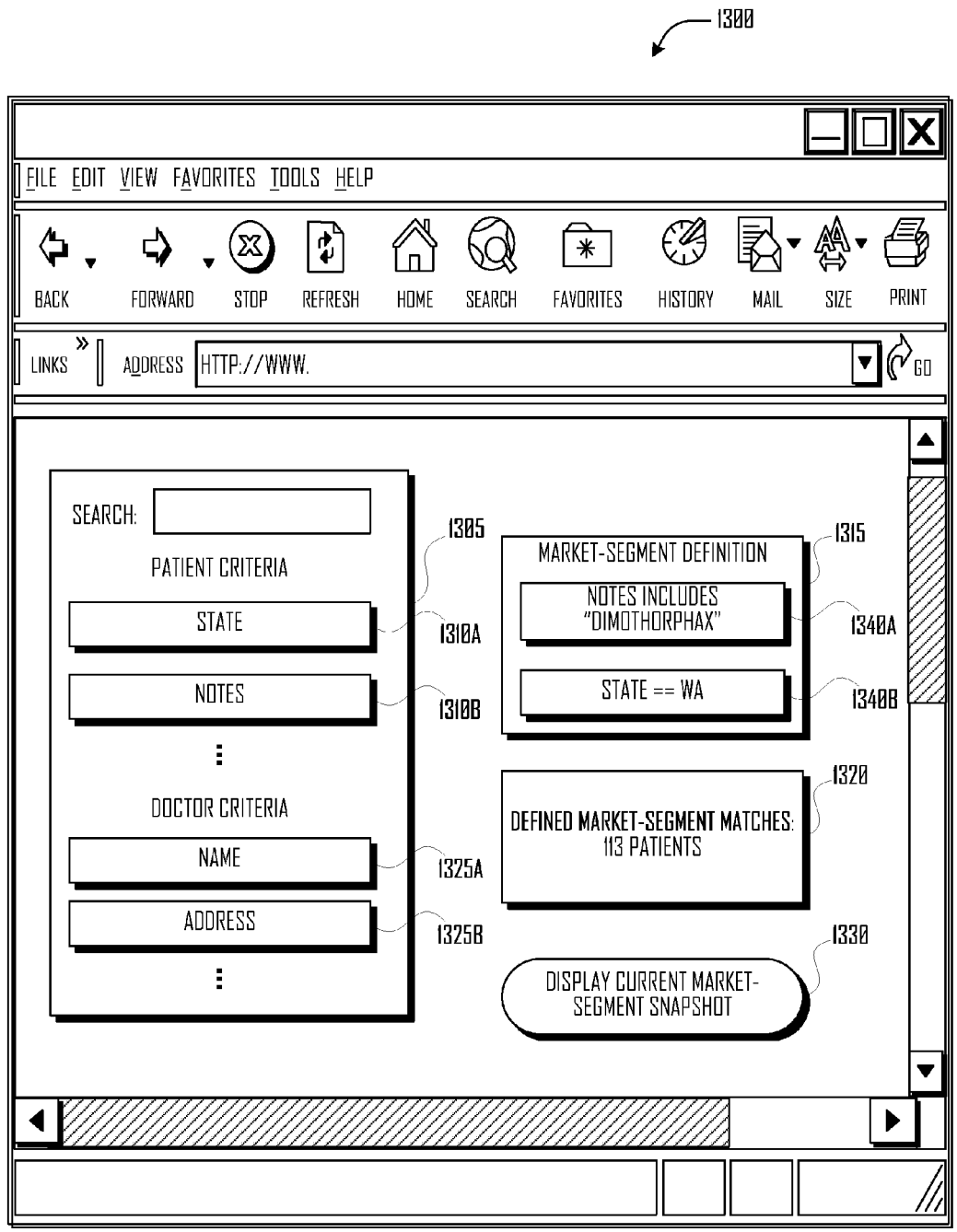
FIG. 13 illustrates an exemplary reduced-complexity marketer graphical user interface in accordance with one embodiment.

FIG. 13 illustrates an exemplary reduced-complexity marketer graphical user interface ("GUI") 1300 in accordance with one embodiment. Marketer GUI 1300 includes a searchable list 1305 of market-segmentation criteria, including criteria 1310A-B for "doctor"-type records (i.e., person-type records) and criteria 1325A-C for "facility"-type records (i.e., entity-type records). As illustrated, no search term is entered in search box 1335. If, however, a user entered a search term (e.g., "name") in box 1335, the list of displayed criteria might include only criteria 1310A and 1325A (doctor name and facility name criteria, respectively).

Marketer GUI 1300 also includes a list 1315 of selected market-segmentation criteria 1340A-B that make up a market-segment definition. In the illustrated example, a marketer has selected two patient criteria 1310A-B and entered desired values for the selected criteria. In one embodiment, a marketer may select market-segmentation criteria 1340A-B for a market-segment definition by dragging a criterion from searchable list 1305 to market-segment-definition list 1315. In other embodiments, a marketer may select market-segmentation criteria by selecting check boxes (not shown) or according to any other method of selection.

Marketer GUI 1300 also includes a market-segment-definition metadata display 1320, which shows information about the market-segment defined by the currently-selected market-segmentation criteria 1340A-B. In the illustrated example, metadata display 1320 shows that data table 120 currently includes 113 patient records that match the marketer-specified criteria (i.e., patients in Washington with notes including "dimothorphax"). In one embodiment, when the marketer adjusts the market-segment definition, the metadata display 1320 may be updated automatically in real-time or near-real-time, thereby enabling the marketer to rapidly home in on a desirable market-segment. Marketer GUI 1300 also includes a control 1330 to display all or part of a current snapshot of the defined market segment.

Figure 14:
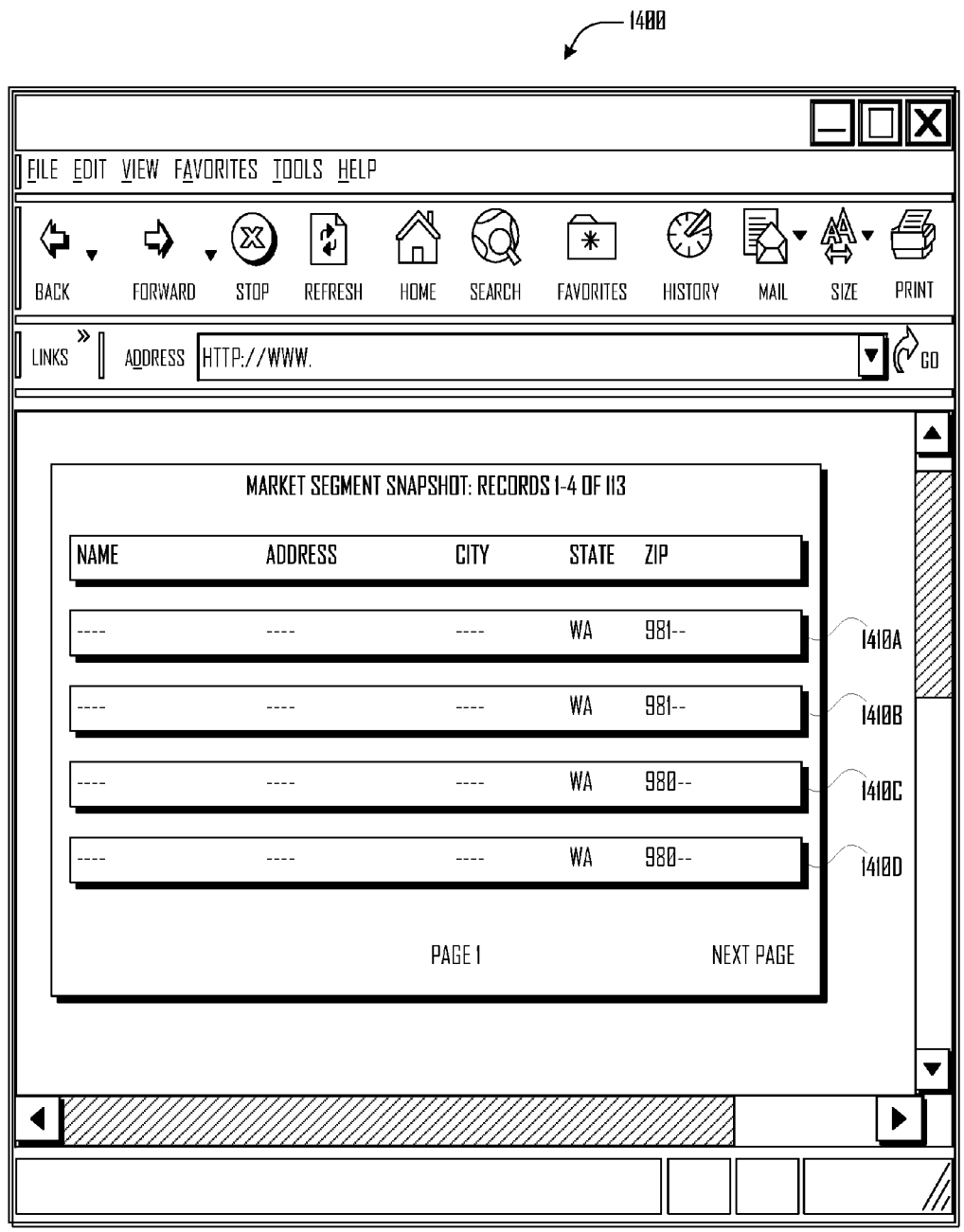
FIG. 14 illustrates an exemplary anonymized result-rows GUI in accordance with one embodiment.

FIG. 14 illustrates an exemplary anonymized result-rows GUI 1400 in accordance with one embodiment. Market-segment snapshot GUI 1400 includes anonymized records 1415A-D.

Although specific embodiments have been illustrated and described herein, a whole variety of alternate and/or equivalent implementations may be substituted for the specific embodiments shown and described without departing from the scope of the present disclosure. This application is intended to cover any adaptations or variations of the embodiments discussed herein.

The invention claimed is:

1. A computer-implemented method for importing protected healthcare marketing data, the method comprising:
    obtaining, by the computer, healthcare-marketing-related plaintext data values structured according to a plurality of source fields of a plurality of field types;
    storing said healthcare-marketing-related plaintext data values into a protected healthcare-marketing data record having a plurality of data fields corresponding respectively to said plurality of source fields, wherein storing said healthcare-marketing-related data into said protected healthcare-marketing data record includes, for each of said plurality of source fields:
        determining, by the computer, whether the current source field is of a PHI type that includes protected health information ("PHI"); and
        when the current source field is determined to be of said PHI type, the computer encrypting the current-source-field plaintext value and storing the current-source-field encrypted value in a corresponding data field of said protected healthcare-marketing data record;
    storing at least some of said healthcare-marketing-related data into a protected healthcare-marketing search record having a plurality of search fields corresponding respectively to at least some of said plurality of source fields, wherein storing at least some of said healthcare-marketing-related data into said protected healthcare-marketing search record includes, for each of said plurality of source fields:
        determining, by the computer, whether the current source field is of a searchable type that includes searchable information; and
        when the current source field is determined to be of said searchable type, the computer deriving a current-source-field hash value from the current-source-field plaintext value and storing said current-source-field hash value in a corresponding search field of said protected healthcare-marketing search record; and associating said protected healthcare-marketing search record with said protected healthcare-marketing data record.

2. The method of claim 1, wherein storing said healthcare-marketing-related data into a protected healthcare-marketing data record further comprises: when the current field is determined to be of a non-PHI type that does not include PHI, storing the current field plaintext value in said corresponding field of said protected healthcare-marketing data record.

3. The method of claim 1, wherein deriving said current-source-field hash value from the current-source-field plaintext value comprises:
conforming the current-source-field plaintext value to a field-type-specific data standard to obtain a standardized plaintext value; and
mapping the resulting standardized plaintext value to said current-source-field hash value using a cryptographic hash function.

4. The method of claim 1, wherein storing at least some of said healthcare-marketing-related data into a protected healthcare-marketing search record further comprises, when the current source field is determined to be of said searchable type:
obtaining a plurality of non-search terms; and
prior to deriving said current-source-field hash value, stripping at least one of said plurality of non-search terms from said current-source-field plaintext value.

5. The method of claim 1, wherein deriving said current-source-field hash value from the current-source-field plaintext value comprises:
identifying a plurality of plaintext searchable terms within said current-source-field plaintext value; and
respectively deriving a plurality of hash values (including said current-source-field hash value) from said plurality of plaintext searchable terms.

6. The method of claim 5, wherein storing said current-source-field hash value in a corresponding search field of said protected healthcare-marketing search record comprises:
respectively storing said plurality of hash values in a plurality of search fields of said protected healthcare-marketing search record, each of said plurality of search fields of said protected healthcare-marketing search record corresponding to the current source field.

7. A non-transient computer-readable storage medium having stored thereon instructions that, when executed by a processor, configure the processor to perform the method of claim 1.

8. A computing apparatus comprising a processor and a memory storing instructions that, when executed by the processor, configure the apparatus to perform the method of claim 1.

9. A computer-implemented method for accessing protected healthcare-marketing data records stored in a healthcare-marketing data table of a healthcare-marketing database, the healthcare-marketing data records each comprising a plurality of healthcare-marketing protected-data fields that include protected health information, the method comprising:
receiving, by the computer from a healthcare-marketer device, a plaintext query describing a set of the healthcare-marketing data records via at least one query predicate comprising a predicate plaintext value and a predicate field identifier corresponding to a data field of said set of healthcare-marketing data records;
determining, by the computer, a hashed query predicate comprising said predicate field identifier and a predicate hash value derived from said predicate plaintext value via a hash function;
using said hashed query predicate, the computer querying a healthcare-marketing search table of said healthcare-marketing database, said healthcare-marketing search table storing healthcare-marketing search records that correspond respectively to the healthcare-marketing data records, said healthcare-marketing search records each comprising a plurality of search fields that respectively correspond to at least some of the plurality of healthcare-marketing protected-data fields, each of said plurality of search fields including a searchable hash value derived via said hash function from a plaintext form of a corresponding one of the healthcare-marketing protected-data fields;
in response to querying said healthcare-marketing search table, the computer receiving from the healthcare-marketing database a set of said healthcare-marketing search results that correspond to said set of the healthcare-marketing data records described by said plaintext query;
using said set of said healthcare-marketing search results, the computer identifying said set of the healthcare-marketing data records from the healthcare-marketing database;
generating, by the computer, a set of anonymized results corresponding to said set of the healthcare-marketing data records; and
in response to receiving said plaintext query, the computer providing said set of anonymized results to said healthcare-marketer device.

10. The method of claim 9, wherein generating said set of anonymized results comprises redacting the protected health information included in the plurality of healthcare-marketing protected-data fields of said set of the healthcare-marketing data records.

11. The method of claim 9, further comprising:
receiving an indication from said healthcare-marketer device to generate a plurality of personalized marketing messages corresponding respectively to said set of anonymized results;
without exposing the protected health information to said healthcare-marketer device, the computer accessing the protected health information associated with said set of the healthcare-marketing data records; and
based at least in part on said indication and on the accessed protected health information, generating said plurality of personalized marketing messages.

12. The method of claim 11, further comprising electronically sending said plurality of personalized marketing messages to a plurality of individuals respectively associated with said set of the healthcare-marketing data records.

13. A non-transient computer-readable storage medium having stored thereon instructions that, when executed by a processor, configure the processor to perform the method of claim 9.

14. A computing apparatus comprising a processor and a memory storing instructions that, when executed by the processor, configure the apparatus to perform the method of claim 9.

* * * * *